United States Patent [19]

de la Guardia

[11] 4,373,540

[45] Feb. 15, 1983

[54] HAIR STRAIGHTENING PROCESS AND HAIR CURLING PROCESS AND COMPOSITIONS THEREFOR

[75] Inventor: Mario J. de la Guardia, Savannah, Ga.

[73] Assignee: Carson Products Company, Savannah, Ga.

[21] Appl. No.: 214,023

[22] Filed: Dec. 8, 1980

Related U.S. Application Data

[62] Division of Ser. No. 805,149, Jun. 9, 1977, Pat. No. 4,304,244.

[51] Int. Cl.$^2$ ............................................. A45D 7/00
[52] U.S. Cl. ....................................... 424/89; 424/89
[58] Field of Search ................ 132/7; 424/70, 71, 89; 252/544

[56] References Cited

U.S. PATENT DOCUMENTS

| | | | |
|---|---|---|---|
| 2,794,440 | 6/1957 | Levie | 132/7 |
| 2,836,543 | 5/1958 | Watson | 132/7 |
| 3,960,782 | 6/1976 | Daley | 252/544 |

OTHER PUBLICATIONS

Cosmetics, Science and Technology, author–Sagarin, E., 1957, pp. 446 and 616.

*Primary Examiner*—G. E. McNeill
*Attorney, Agent, or Firm*—Newton, Hopkins & Ormsby

[57] ABSTRACT

Compositions and methods for curling hair and for straightening hair are disclosed, wherein the compositions contain, as the principal active ingredient thereof, guanidine hydroxide. The guanidine hydroxide may be conveniently prepared by reacting calcium hydroxide and guanidine carbonate.

Hair is curled by contacting the hair with the composition while the hair is on curlers, or otherwise maintained in a curled configuration. After the desired treatment time, the hair is rinsed and neutralized, with long lasting curls of the so-called "permanent wave" nature resulting.

Hair may be straightened by contacting the hair with the composition and maintaining the hair in a generally straight configuration over at least a portion of the time that the hair is contacted by the composition. Thereafter the hair may be rinsed and neutralized.

2 Claims, No Drawings

HAIR STRAIGHTENING PROCESS AND HAIR CURLING PROCESS AND COMPOSITIONS THEREFOR

This is a divisional application of Ser. No. 805,149, filed June 9, 1977, now U.S. Pat. No. 4,304,244, issued Dec. 8, 1981.

BACKGROUND OF THE INVENTION

Commercial products based upon compositions containing thioglycolates, sulfites or alkali metal hydroxides, such as sodium hydroxides, have been widely used to permanently straighten unstraight hair, especially to straighten unstraight Negro hair. Of these products, the thioglycolate compositions and the sulfite compositions which have been commercially marketed have been relatively ineffective, with the hair in many cases reverting at least partially to the original unstraight form. While very effective in producing the desired straightening effect, sodium hydroxide compositions are very harsh to both the scalp and the hair, and the use of such compositions has resulted in numerous instances of scalp irritation and/or burning, and has also resulted in a substantial reduction of the strength of the treated hair, and even, in some instances, considerable hair loss.

Various guanidine compounds have been evaluated by the prior art in hair waving or hair straightening compositions. Of these guanidine thioglycolate appears to have had the most attention by researchers in this art. See, for example, Shansky, *American Perfumer and Cosmetics*, Volume 78, August, 1963, 32–34; Bogaty et al, *American Perfumer and Cosmetics*, Volume 78, November, 1963, pages 45–47; and Shansky, *American Perfumer and Cosmetics*, Volume 78, December, 1963, pages 29–30.

Various organic bases including guanidine have been found to accelerate the dehairing effect of calcium hydroxide suspensions. See, e.g. Barry, "Delipatories" *Cosmetic Science and Technology*, Edited by Balsam and Sagarin, 2nd Edition, Volume 2, Chapter 18, page 39, 45, Wiley Interscience, New York, 1972 and Barry "Depilatories" *Cosmetic Science and Technology*, Edited by Sagarin, First Edition, Chapter 20, page 461–462, Interscience Publishers, New York, 1957, and references cited therein.

U.S. Pat. No. 3,157,578, Nov. 17, 1964, discloses compositions for the permanent waving of human hair utilizing a solution containing, e.g. thioglycollic acid and guanidine carbonate. These compositions are employed in the form of aqueous solutions having a pH value of from 7–9, with the guanidine used to replace ammonia used previously thereto, both to function as a neutralizing agent for the acid reducing agent, and also in the form of ammonium carbonate for pH control.

U.S. Pat. No. 3,861,868 of Jan. 21, 1975 acknowledges, in column 1 thereof, earlier abandoned applications relating to the use of guanidine salts in hair dying compositions and hair bleaching compositions.

British Pat. No. 1,274,565 of May 17, 1972 discloses a process for the straightening of human hair wherein the hair straightening is conducted in two separate stages. In the first stage, a known keratin softening substance, such as an alkali hydroxide, sulfite or bisulfite, or a salt of a mercaptocarboxylic acid, is permitted to act upon the hair. After the extensive removal of the keratin softening component, a media containing a swelling substance is applied to the hair. Suitable swelling agents include monovalent aliphatic alcohol, aromatic alcohols, aliphatic diols, ether alcohols, sulfoxides, sulfones, thiocyanates, thiourea and urea, and water-soluble derivatives thereof.

U.S. Pat. No. 3,865,930 of Feb. 11, 1975 discloses a permanent wave composition based on a two-stage operation, wherein in the first stage the S-S linkages of the keratin fiber are opened at an alkaline pH with the addition of a reducing agent such as a thiol. The hair is then treated in a second stage with an oxidizing or neutralizing agent to reconstitute the S-S bridges, so as to impart to the hair the desired configuration. The patent relates to a composition for the aforesaid second stage, wherein the S-S bridges are reformed. This composition is a two-component composition, with one component based on a water-soluble sulfite, bisulfite, metabisulfite or thiourea, and the other component is hydrogen peroxide.

U.S. Pat. Nos. 2,817,342 of Dec. 24, 1957 and 2,840,086 of June 24, 1958 relate to permanent waving compositions based upon sulfite-type materials. Among other acid sulfites disclosed are an acid solution of guanidine bisulfite, formed by bubbling sulfur dioxide gas into an aqueous solution of guanidine carbonate.

Japanese Pat. No. 76-9013 discloses hair waving or straightening treatments wherein the hair is initially treated with a weak alkali, followed by a treatment with a chelating metallic salt solution. Calcium oxide or calcium hydroxide is used as a chelating agent to prevent mutual interactions of the active ingredients.

U.S. Pat. No. 2,836,543 of May 27, 1954 discloses the use of guanidine as a swelling agent component in a hair setting composition. The composition also includes a water-soluble sulfite and a polyfunctional aromatic additive compound, such as genetistic acid, which acts as an accelerator.

U.S. Pat. No. 3,642,429 of Feb. 15, 1972 is directed to a hair treatment composition based on a polycondensate of methylol compounds and an urein compound. The generic formula for the urein compound appears to encompass guanidine, but guanidine is not named in that patent.

U.S. Pat. No. 3,686,296 is directed to depilatories which are nitrogen-based thioglycerol molecular complexes. The nitrogen base may be, e.g. guanidine or guanidine hydrochloride.

SUMMARY OF THE INVENTION

The present invention is based upon the discovery that human hair straightening or relaxing compositions, which exhibit improved hair strength retention and significantly reduced scalp irritation, compared to relaxing compositions based upon alkali metal hydroxides, may be formulated with the use of guanidine hydroxide as the principal active ingredient. These compositions exhibit so-called "permanent relaxation", a relaxing effect which lasts until new hair growth requires the repetition of treatment.

The hair is preferably treated by applying thereto the aqueous reaction product formed by reacting, in an aqueous medium, at least one water-soluble inorganic hydroxide, preferably an alkaline earth metal hydroxide, such as calcium hydroxide, and at least one water-soluble guanidine salt, such as guanidine carbonate. After a suitable time, conveniently about 5 to 45 minutes, the composition is removed from the hair. Preferably, the treated hair is fixed or neutralized while the hair is maintained in a substantially straightened configuration. Generally the pH value of the hair will be reduced to no greater than about 7 during this step, and preferably the pH of the hair is reduced to about 5.0 to 6.5, although lower pH values may be used if desired.

Furthermore, the guanidine hydroxide compositions have been found to be surprisingly effective in so-called "permanent wave" applications, wherein such compositions exhibit the same advantages of effectiveness, reduced irritability, and high strength retention, as noted for the hair relaxer compositions of this invention. Also, the sulfur dioxide, mercaptan, and/or ammonia smell noticed with conventional, commercial waving compositions will not be noticed with the compositions of the present invention. The guanidine hydroxide is preferably formed by reacting the aforesaid hydroxide and the aforesaid guanidine salt in an aqueous medium, and the resulting aqueous reaction product is applied to curled hair, Preferably the hair is deformed during the treatment time by being maintained on curlers.

After the desired treatment time with the guanidine hydroxide composition has elapsed, the composition is removed from the hair and/or the hair is neutralized with a neutralizing solution, such as an acidic shampoo. The curlers may be removed from the hair for the rinsing and neutralizing steps, or these steps may be accomplished while the hair is maintained on curlers, as is known to the art. Thereafter, the hair will normally be dried using a blow dryer.

DETAILED DESCRIPTION OF THE INVENTION

Hair Relaxing Composition and Method

Unstraight hair is straightened by contacting the hair with a straightening amount of an aqueous setting composition, and straightening the hair during at least a portion of the time the composition is in contact therewith. The straightening composition is preferably formed by reacting in an aqueous medium at least one water-soluble inorganic hydroxide with at least one guanidine salt, the anion of which forms a substantially water-insoluble salt with the cation of the hydroxide.

The preferred straightening composition of the present invention is a two-component composition, as the resulting aqueous reaction product has only limited shelf stability under normal conditions. One of the components is a water-soluble hydroxide, preferably a hydroxide which is at least as soluble in water as calcium hydroxide. Lithium hydroxide may be used, but the preferred hydroxides are alkali metal hydroxides, especially calcium, barium or strontium hydroxide or mixtures thereof. Availability, cost and effectiveness make calcium hydroxide the most preferred hydroxide. It should be pointed out that the oral toxicity of barium hydroxide makes that hydroxide much less preferred than calcium hydroxide.

It appears that the reaction between the inorganic hydroxide and the guanidine salt is an equilibrium reaction, and if the anion of the guanidine salt does not form a substantially water-insoluble salt with the cation of the hydroxide, then the reaction to produce guanidine hydroxide will not be driven towards completion. For this reason, it is critical that the anion of the guanidine salt form a substantially water-insoluble salt with the cation of the inorganic hydroxide. As indicated above, lithium hydroxide can be used but is not preferred, as the salt produced by the reaction with, e.g. guanidine carbonate, while relatively insoluble, is not insoluble to the same degree as the salt produced by the reaction of an alkaline earth metal hydroxide with guanidine carbonate. The other alkali metal hydroxides have carbonate salts which are just too water soluble to drive the reaction towards completion. Thus, the salt produced by the reaction of the inorganic hydroxide and the guanidine salt should be at least as water-insoluble as lithium carbonate, and, as indicated, the alkaline earth metal hydroxides are decidedly preferred.

The other component is a water-soluble guanidine salt, the anion of which forms a substantially water-insoluble salt with the cation of the hydroxide. This water insoluble salt should be no more soluble than lithium carbonate, and preferably has less water solubility than lithium carbonate. Preferred guanidine salts are guanidine carbonate and guanidine sulfate, and of these guanidine carbonate is especially preferred.

One or both of the components may be in the form of an aqueous solution, or both components may be in non-aqueous form, with water additionally added to the admixed components. Under certain circumstances, the components may be stable in their admixed solid form, and in such situation the two ingredients could be marketed as a single component, to which water is added in order to generate the desired reaction. However, it is decidedly preferred that the hydroxide and the guanidine salt be packaged as separate components, especially with each component in the form of an aqueous solution, as the resulting mixing of the components is greatly facilitated thereby.

Preferably the two components are reacted together at substantially ambient conditions, although elevated or reduced temperature could be utilized if desired. Normally, however, the reaction temperature will be no lower than 35° F. and no higher than 140° F., as no advantage will be gained by working outside of this range.

After the two components are admixed in an aqueous system, the resulting hair relaxing compositions should be used within about 48 hours, due to the relative instability of guanidine hydroxide solutions exposed to ambient conditions.

It is greatly preferred that the hydroxide be present in at least a stoichiometric amount, based upon the amount of guanidine salt present in the admixture. More preferably the hydroxide is present in an amount equal to 2-5 times the stoichiometric amount, although this is not critical. The composition with the above-noted amounts of hydroxide is generally above the hydroxide solubility level, so that amounts substantially in excess of this range may be used without causing undue difficulties. However, if the hydroxide is present in a cream base, the cream form may be unstable due to the presence of too much inorganic hydroxide, e.g., calcium hydroxide, which could form a gritty texture and might cause undesired deposits upon the hair.

Less than stoichiometric amounts of inorganic hydroxide may be used, but then the system will be less effective, and it is strongly preferred that an excess of hydroxide be used in order to scavenge any carbon dioxide that may be present, to thereby minimize unwanted formation of guanidine carbonate in the reaction product. Within these broad parameters, however, the amount of inorganic hydroxide used is not critical.

Conventional additives may be present in the compositions of the present invention in order to provide their known functions therein. For instance, the inorganic hydroxide may be in an aqueous cream component, containing an emulsifier, a thickener, an emollient and/or a humectant. Preservatives may be added and accelerators may be presented, especially if low concentrations of the reaction product are utilized.

Thorough mixing of the ingredients, especially when one is in a cream or emulsion form, is strongly recommended. The reaction between the hydroxide and the guanidine salt generally proceeds rapidly upon adequate mixing, and is normally substantially complete within a few minutes time.

The principal active ingredient in the above-described reaction product appears to be guanidine hydroxide. The reaction products are not susceptible to easy identification of the compounds therein, but guanidine hydroxide has been made by other methods (wherein its presence has been confirmed) and tested for hair relaxing ability, which was found to be substantially the same as for the aqueous reaction product formed by reacting the inorganic hydroxide and the guanidine salt.

The guanidine hydroxide in an aqueous guanidine hydroxide solution tends to be converted to guanidine carbonate upon exposure to atmospheric carbon dioxide, so that stability problems will be noted unless special precautions are taken. However, it appears possible to duplicate the results obtained with the two-component system described hereinabove by using dry guanidine hydroxide, which can be incorporated into an aqueous solution shortly prior to use. Again, conventional additives may be added to such guanidine hydroxide solution.

Higher concentrations of guanidine hydroxide in the relaxer composition raises the possibility of greater scalp irritation and more hair damage. The treatment time can generally be reduced with such higher concentrations, so that if adequate care is taken, as may be the case in commercial beauty shop operations, to minimize exposure, such higher concentrations may be utilized. In general, the amount of guanidine hydroxide in the relaxer composition can vary from about 1% by weight to about 50% by weight, based on the total weight of the composition. Concentrations below about 1% by weight are generally too dilute to be effective, and concentrations of guanidine hydroxide above about 50% by weight generally exceed the solubility limit. It is greatly preferred that the guanidine hydroxide concentration be within the range of 2% to 20% by weight, based on the total weight of the composition. More preferably, the guanidine hydroxide concentration is in the range of 3-10% by weight, and most preferably the guanidine hydroxide concentration is from 4-7% by weight, based on the total weight of the composition.

When a two-component system is used, the individual components may vary from a solid component to a very dilute solution or dispersion. The guanidine salt will preferably be in the form of an aqueous solution having at most about 40% by weight of the guanidine salt, preferably less than 35% by weight, and generally having at least about 1.2% by weight of the guanidine salt. Aqueous components containing more than 50% by weight of the inorganic hydroxide are difficult to handle, and it is preferred that that component contain less than 30% by weight of inorganic hydroxide. Generally at least 1.5% by weight of the inorganic hydroxide will be used, and preferably the inorganic hydroxide is in an aqueous component in an amount of 4 to 15% by weight, more preferably about 5 to 8% by weight. It will be readily appreciated, however, that an increase or decrease in the concentration of one component may be compensated by appropriate adjustments to the concentration of the other ingredient, and to the ratio of the two ingredients in the final formulation. The important item, however, is the concentration of the resulting guanidine hydroxide in the final formulation, and that concentration should be within the ranges set forth above.

It is contemplated that commercial compositions based upon this development will be a two-component system containing 5.4–5.6% by weight guanidine carbonate and 5.75–6.0% by weight of calcium hydroxide, based on the total weight of the relaxer composition.

As applied to the hair, the relaxer composition of the present invention will not contain any sulphur-based keratin-breaking agents, and preferably does not contain, as applied to the hair, any organic sulphur-containing compounds. As indicated, thiourea can be utilized as an accelerator, but this is normally unnecessary and not preferred. Normally, the only sulphur-containing compound in the two-component composition of the present invention might be guanidine sulfate, and the sulfate would be reacted with the inorganic hydroxide to produce an insoluble inorganic sulfate, such as calcium sulfate, which would not be an active agent in the hair relaxing treatment. Thus, the composition of the present invention can be readily distinguished from the prior art compositions based upon thioglycolates or sulfites.

At lower levels of guanidine hydroxide in the relaxer formulation, it may be preferred to use an accelerator, such as thiourea, in order to obtain adequate hair relaxing within acceptable treatment times. Thiourea functions as an accelerator at low levels of guanidine hydroxide, but this effect appears to be a rate acceleration and the acceleration effect is generally not seen when higher, preferred guanidine hydroxide concentrations are utilized, as the hair relaxing appears to be complete within normal treatment times, even without the presence of the thiourea or other accelerator.

When the relaxer composition is in the form of a two-component system, the aqueous solution of the water-soluble product of the reaction of the two components should have a higher pH value than the pH of solutions of either the inorganic hydroxide or the guanidine salt. The reaction product (that is, the relaxer composition which is applied to the hair) should have a pH value above 11.8, preferably about 12.5 to about 13.5, and more preferably around 13.0.

The time of treatment of hair to be relaxed with the relaxer formulation of the present invention will normally be within the range of 5–45 minutes, with the time starting from the first application of the relaxer composition to the hair. Generally this treatment time will be at least 10 minutes, and there is no real upper limit on the time that the composition can remain on the hair, with the above-noted 45 minute time generally being about the greatest length of time that is commercially acceptable to end users. It is greatly preferred to utilize no more than about 30 minutes, preferably less than 25 minutes, of treatment time, and more preferably the treatment time is in the neighborhood of 20 minutes.

After the above treatment time has elapsed, the relaxer composition should be removed from the hair in order to prevent further decrease of the strength retention of the treated hair. A major portion of the relaxer composition can be removed from the hair by thorough rinsing. It is preferred that the rinsing be followed by a neutralizing step, using any suitable neutralizing agent.

A buffered neutralizing shampoo has been found to be effective, but any conventional neutralizing methods and compositions, well known to the art, may be utilized. For instance, citric acid may be added to a conventional shampoo until the pH of the acidified shampoo has been reduced to 5.0 to form an effective neutralizing shampoo. Preferably the hair is neutralized by reducing the pH thereof to a value of no greater than about 7, and more preferably to a value of about 5.0–6.5. While lower pH values may be used, it is generally preferred to maintain the pH of the treated hair within the range of about 5.0 to about 7.0.

Generally the composition will be applied to the hair at ambient temperatures, but the composition may be at a temperature of 35°–140° F. if desired. No advantages will be obtained by working outside of this range.

Hair Curling Composition and Method

Hair is curled or waved by contacting the hair with a curling amount of an aqueous waving composition, and curling the hair during at least a portion of the time the composition is in contact therewith. The waving composition is preferably formed by reacting in an aqueous medium at least one water-soluble inorganic hydroxide with at least one guanidine salt, the anion of which forms a substantially water-insoluble salt with the cation of the hydroxide.

The preferred waving composition of the present invention is a two-component composition, as the resulting aqueous reaction product has only limited shelf stability under normal conditions. One of the components is a water-soluble inorganic hydroxide, preferably a hydroxide which is at least as soluble in water as calcium hydroxide. Lithium hydroxide may be used, but the preferred hydroxides are alkali metal hydroxides, especially calcium, barium or strontium hydroxide or mixtures thereof. Availability, cost and effectiveness make calcium hydroxide the most preferred hydroxide.

It should be pointed out that the oral toxicity of barium hydroxide makes that hydroxide much less preferred than calcium hydroxide.

It appears that the reaction between the inorganic hydroxide and the guanidine salt is an equilibrium reaction, and if the anion of the guanidine salt does not form a substantially water-insoluble salt with the cation of the hydroxide, then the reaction to produce guanidine hydroxide will not be driven towards completion. For this reason, it is critical that the anion of the guanidine salt form a substantially water-insoluble salt with the cation of the inorganic hydroxide. As indicated above, lithium hydroxide can be used but is not preferred, as the salt produced by the reaction with, e.g. guanidine carbonate, while relatively insoluble, is not insoluble to the same degree as the salt produced by the reaction of an alkaline earth metal hydroxide with guanidine carbonate. The other alkali metal hydroxides have carbonate salts which are just too water soluble to drive the reaction towards completion. Thus, the salt produced by the reaction of the inorganic hydroxide and the guanidine salt should be at least as water-insoluble as lithium carbonate, and, as indicated, the alkaline earth metal hydroxides are decidedly preferred.

The other component of the waving composition is a water-soluble guanidine salt, the anion of which forms a substantially water-insoluble salt with the cation of the hydroxide. This water-insoluble salt should be no more soluble than lithium carbonate, and preferably has less water solubility than lithium carbonate. Preferred guanidine salts are guanidine carbonate and guanidine sulfate, and of these guanidine carbonate is especially preferred.

One or both of the components may be in the form of an aqueous solution, or both components may be in non-aqueous form with water additionally added to the admixed components. Under certain circumstances, the components may be stable in their admixed solid form, and in such situation the two ingredients could be marketed as a single component, to which water is added in order to generate the desired reaction. However, it is decidedly preferred that the hydroxide and the guanidine salt be packaged as separate components, especially with each component in the form of an aqueous solution, as the resulting mixing of the components is greatly facilitated thereby.

Preferably the two components are reacted together at substantially ambient conditions, although elevated or reduced temperatures could be utilized if desired. Normally, however, the reaction temperature will be no lower than 35° F. and no higher than 140° F., as no advantage will be gained by working outside of this range.

After the two components are admixed in an aqueous system, the resulting hair waving composition should be used within about 48 hours, due to the relative instability of guanidine hydroxide solutions exposed to ambient conditions.

It is greatly preferred that the hydroxide be present in at least a stoichiometric amount, based upon the amount of guanidine salt present in the admixture. More preferably the hydroxide is present in an amount equal to 2–5 times the stoichiometric amount, although this is not critical. The composition with the abovenoted amounts of hydroxide is generally above the hydroxide solubility level, so that amounts substantially in excess of this range may be used without causing undue difficulties. However, if the hydroxide is present in an emulsified base, the cream or emulsion form may be unstable due to the presence of too much inorganic hydroxide, e.g., calcium hydroxide, which could form a gritty texture and might cause undesired deposits upon the hair.

Less than stoichiometric amounts of inorganic hydroxide may be used, but then the waving composition will be less effective, and it is strongly preferred that an excess of hydroxide be used in order to scavenge any carbon dioxide that may be present, to thereby minimize unwanted formation of guanidine carbonate in the reaction product. Within these broad parameters, however, the amount of inorganic hydroxide used is not critical.

Conventional additives may be present in the compositions of the present invention in order to provide their known functions therein. Preservatives, emulsifiers, and/or humectants may be added and accelerators may be present especially if low concentrations of the reaction product are utilized. Generally, the hair waving compositions of this invention will have lower viscosities than the hair relaxing compositions described herein as the waving composition may be applied to curled hair wherein the composition must penetrate into the curl.

Thorough mixing of the ingredients, especially if one component is in a cream or emulsion form, is strongly recommended. The reaction between the hydroxide and the guanidine salt generally proceeds rapidly upon adequate mixing, and is normally substantially complete within a few minutes time.

The principal active ingredient in the above-described reaction product appears to be guanidine hydroxide. The reaction products are not susceptible to easy identification of the compounds therein, but guanidine hydroxide has been made by other methods (wherein its presence has been confirmed) and tested for hair curling ability, which was found to be substantially the same as for the aqueous reaction product formed by reacting the inorganic hydroxide and the guanidine salt.

The guanidine hydroxide in an aqueous guanidine hydroxide solution tends to be converted to guanidine carbonate upon exposure to atmospheric carbon dioxide, so that stability problems will be noted, unless special precautions are taken to exclude carbon dioxide. However, it appears possible to duplicate the results obtained with the two-component hair curling system described hereinabove by using dry guanidine hydroxide, which can be incorporated into an aqueous solution shortly prior to use. Again, conventional additives may be added to such guanidine hydroxide solution.

Higher concentrations of guanidine hydroxide in the hair curling composition raises the possibility of greater scalp irritation and more hair damage. The treatment time can generally be reduced with such higher concentrations, so that if adequate care is taken, as may be the case in commercial beauty shop operations, to minimize exposure, such higher concentrations may be utilized. In general, the amount of guanidine hydroxide in the hair curling composition can vary from about 1% by weight to about 50% by weight, based on the total weight of the compositon. Concentrations below about 1% by weight are generally too dilute to be effective, and concentrations of guanidine hydroxide above about 50% by weight generally exceed the solubility limit. It is greatly preferred that the guanidine hydroxide concentration be within the range of 2% to 20% by weight, based on the total weight of the composition. More preferably, the guanidine hydroxide concentration is in the range of 3-10% by weight, and most preferably the guanidine hydroxide concentration is from 4-7% by weight, based on the total weight of the composition.

When a two-component system is used, the individual components may vary from a solid component to a very dilute solution or dispersion. The guanidine salt will preferably be in the form of an aqueous solution having at most about 40% by weight of the guanidine salt, preferably less than 35% by weight, and generally having at least about 1.2% by weight of the guanidine salt. Aqueous components containing more than 50% by weight of the inorganic hydroxide are difficult to handle, and it is preferred that that component contain less than 30% by weight of inorganic hydroxide. Generally at least 1.5% by weight of the inorganic hydroxide will be used, and preferably the inorganic hydroxide is in an aqueous component in an amount of 4 to 15% by weight, more preferably about 5 to 8% by weight. It will be readily appreciated, however, that an increase or decrease in the concentration of one component may be compensated by appropriate adjustments to the concentration of the other ingredient, and to the ratio of the two ingredients in the final formulation. The important item, however, is the concentration of the resulting guanidine hydroxide in the final formulation, and that concentration should be within the ranges set forth above.

As applied to the hair, the hair curling composition of the present invention will not contain any sulphur-based keratin-breaking agents, and preferably does not contain, as applied to the hair, any organic sulphur-containing compounds. As indicated, thiourea can be utilized as an accelerator, but this is normally unnecessary and not preferred. Normally, the only sulphur-containing compound in the two-component composition of the present invention might be guanidine sulfate, and the sulfate would be reacted with the inorganic hydroxide to produce an insoluble inorganic sulfate, such as calcium sulfate, which would not be an active agent in the hair curling treatment. Thus, the composition of the present invention can be readily distinguished from prior art compositions based upon thioglycolates or sulfites.

At lower levels of guanidine hydroxide in the relaxer formulation, it may be preferred to use an accelerator, such as thiourea, in order to obtain adequate hair relaxing within acceptable treatment times. Thiourea functions as an accelerator at low levels of guanidine hydroxide, but this effect appears to be a rate acceleration and the acceleration effect is generally not seen when higher, preferred guanidine hydroxide concontrations are utilized, as the hair curling appears to be complete within normal treatment times, even without the presence of the thiourea or other accelerator.

When the hair curling composition is in the form of a two-component system, the aqueous solution of the water-soluble product of the reaction of the two components should have a higher pH value than the pH of solutions of either the inorganic hydroxide or the guanidine salt. The reaction product (that is, the hair curling composition which is applied to the hair) should have a pH value above 11.8, preferably about 12.5 to about 13.5, and more preferably around 13.0.

The time of treatment of hair to be curled or waved with the curling formulation of the present invention will normally be within the range of 5–45 minutes, with the time starting from the first application of the curling composition to the hair. Generally this treatment time will be at least 10 minutes, and there is no real upper limit on the time that the composition can remain on the hair, with the above-noted 45 minute time generally being about the greatest length of time that is commercially acceptable to end users. It is greatly preferred to utilize no more than about 30 minutes, preferably less than 25 minutes, of treatment time, and more preferably the treatment time is in the neighborhood of 20 minutes.

After the above treatment time has elapsed, the curling composition should be removed from the hair in order to prevent further decrease of the strength retention of the treated hair. A major portion of the curling composition can be removed from the hair by thorough rinsing. It is preferred that the rinsing be followed by a neutralizing step, using any suitable neutralizing agent. A buffered neutralizing shampoo has been found to be effective, but any conventional neutralizing methods and compositions, well known to the art, may be utilized. For instance, citric acid may be added to a conventional shampoo until the pH of the acidified shampoo has been reduced to 5.0 to form an effective neutralizing shampoo. Preferably the hair is neutralized by reducing the pH thereof to a value of no greater than about 7, and more preferably to a value of about 5.0–6.5. While lower pH values may be used, it is generally preferred to maintain the pH of the treated hair within the range of about 5.0 to about 7.0.

The curling composition may be removed from the hair by rinsing, and the rinsing step followed by the above-mentioned neutralizing step, by removing the curlers from the hair and rinsing and neutralizing the hair while the hair is in the unrestrained state. In such case the hair must be rewound on curlers after the neutralizing step and maintained in the curled configuration during drying. Alternatively, and in accordance with normal recommended usage of commercially available hair curling compositions, the hair may be maintained on the curler during the rinsing and neutralizing steps. In this instance the neutralizing composition should be of relatively low viscosity in order to adequately penetrate the curled hair. After these steps have been accomplished, the hair may be blown dry and then the curlers removed.

Generally the composition will be applied to the hair at ambient temperatures, but the composition may be at a temperature of 35°-140° F. if desired. No advantages will be obtained by working outside of this range.

The hair curling composition of the present invention produces long-lasting curls of the "permanent wave" nature.

The commercial hair curling compositions now on the U.S. market appear to be based upon ammonium thioglycolate or sodium sulfite and/or ammonium sulfite. These compositions produce a decidedly unpleasant odor of mercaptans, ammonia, and/or sulfur dioxide. In addition to the advantages described hereinabove for the hair curling compositions of the present invention, another decided advantage is freedom from such objectionable odors.

EXAMPLES OF THE INVENTION

EXAMPLE 1

A hair relaxer two-component system was formulated, with one component being in the form of a cream emulsion having the following formulation:

| Ingredient | Weight Percent |
| --- | --- |
| Emulsifier-Cetomacrogol wax (polyethyleneglycol ether of cetyl alcohol) | 10 |
| Thickener-cetyl alcohol | 2.5 |
| Emollient-mineral oil | 20.0 |
| Humectant-propylene glycol | 5.0 |
| Hydroxide-calcium hydroxide | 7.2 |
| Deionized Water | to 100.00 |

The other component of this example was a 25% aqueous solution of guanidine carbonate.

The cream emulsion and the guanidine carbonate solution were admixed under ambient conditions in a weight ratio of 75:25 of cream emulsion: guanidine carbonate solution. A spatula was used to form a hollow in the cream emulsion, and the guanidine carbonate solution was added to the cream. The spatula was used to mix the cream and liquid together thoroughly, scraping the sides and bottom of the mixing container, until the resulting relaxer composition was creamy and free of lumps. This mixing took about two minutes.

The hair of a Negro individual to be treated was gently combed to remove tangles, and then the hair was sectioned, and a generous amount of the relaxer formulation was applied to the hair on a section-by-section basis. The hair was combed gently after the relaxer was applied to insure even distribution, with care taken to avoid pulling or stretching the hair. When the entire head appeared to be covered by the relaxer cream formulation, the hair was parted with a comb in different areas of the head and checked to insure that the relaxer formulation had penetrated to the hair root area. Thereafter, all of the hair was smoothed down, from front to back, using hands or the back of a plastic comb.

The timing of the length of hair relaxer application was started from the moment of first application of the relaxer formulation, and the hair was treated for 15-20 minutes. For coarser textures than the medium-textured individual tested, the maximum recommended time would be 20-25 minutes, whereas for individuals with finer hair, a treatment time of 10-15 minutes might suffice. It has generally been noted that porous hair or hair that has been colored requires less time than normal hair.

After the desired treatment time had elapsed, the hair was rinsed thoroughly with warm water and the hair was then neutralized to approximately a neutral pH by shampooing with a buffered neutralizing shampoo of the following composition:

| Ingredient | Weight Percent |
| --- | --- |
| Triethanolamine lauryl sulfate | 15 |
| Sodium phosphate monobasic | 1.15 |
| Sodium hydroxide | 0.093 |
| Preservatives | 0.35 |
| Deionized water | to 100 |

The neutralizing shampoo had a pH of 6.50 and a buffer capacity of 2.19 milliliters of 0.10 N NaOH per gram of shampoo.

The shampooing involved two lather and rinse cycles, and after the shampooing step the hair was optionally treated with a protein conditioner. After a final rinse the hair was towelled dry and set.

The hair treated in this example had a permanent relaxing or straightening effect, which lasted until new growth appeared at the hair roots. The application of the relaxer composition to the individual's scalp, ears, and other parts of the body resulted in greatly reduced complaints of skin irritation and burning sensations, compared to hair relaxing with commercially available products.

EXAMPLE 2

Example 1 was repeated, except for the presence in the relaxer cream component of 5% by weight of thiourea as an accelerator. The relaxer cream component was mixed with the guanidine carbonate solution in a weight ratio of 85:15 of cream:solution, and applied to the hair of Negro individuals with results similar to those of Example 1.

EXAMPLE 3

Example 1 was repeated, using a cream emulsion: guanidine carbonate solution weight ratio of 70:30, with generally similar results.

EXAMPLE 4

Example 1 was repeated, using a cream emulsion: guanidine carbonate solution weight ratio of 90:10, with generally similar but not as effective results.

EXAMPLE 5

This example relates to a two-component hair relaxer formulation, with a relaxer cream component having the following composition:

| Ingredient | Weight Percent |
| --- | --- |
| Emulsifier: Brij 78 (polyethylene glycol ether of stearyl alcohol) | 5.2 |
| Emulsifier: Myrj 52 (polyethylene glycol ether of steric acid) | 1.3 |
| Thickener-cetyl alcohol | 5.6 |
| Emollient-mineral oil | 20.8 |
| Preservative-propylparaben | 0.05 |
| Preservative-methylparaben | 0.15 |
| Humectant-propylene glycol | 4.0 |
| Hydroxide-calcium hydroxide | 7.2 |
| Deionized water | 55.7 |

The second component had the following composition:

| Ingredient | Weight Percent |
| --- | --- |
| Guanidine carbonate | 25 |
| Water | 75 |

The relaxer cream and the guanidine carbonate solution were mixed together following the procedure of Example 1 in a weight ratio of 75:25 of relaxer cream:-guanidine carbonate solution.

The medium texture hair of Negro individuals was treated with the admixed relaxer composition of this Example, following the procedures of Example 1, with generally similar results.

EXAMPLE 6

This example relates to a two-component relaxer composition utilizing guanidine sulfate. The inorganic hydroxide was in the form of a relaxer cream having the following composition:

| Ingredient | Weight Percent |
| --- | --- |
| Emulsifier-Cetomacrogol wax | 12.0 |
| Emollient-petrolatum | 7.0 |
| Emollient-anyhdrous lanolin | 5.0 |
| Emollient-mineral oil | 16.0 |
| Preservative-methylparaben | 0.15 |
| Preservative-propylparaben | 0.05 |
| Surfactant-Duponol XL (an amphoteric anionic surfactant made by duPont) | 3.0 |
| Humectant-propylene glycol | 5.0 |
| Hydroxide-calcium hydroxide | 15.0 |
| Water | 36.8 |

The other component had the following composition:

| Ingredient | Weight Percent |
| --- | --- |
| Guanidine sulfate | 30 |
| Water | 70 |

The above components were mixed together, following the procedure of Example 1, in a weight ratio of 79:21 of relaxer cream-guanidine sulfate solution, and then used to straighten the hair of Negro individuals, having hair of medium texture, with the hair being relaxed but not as effectively as in Example 1.

EXAMPLE 7

This example relates to the use of strontium hydroxide in a two-component hair relaxer formulation. The relaxer cream component was formulated as follows:

| Ingredient | Weight Percent |
| --- | --- |
| Emulsifier-Cetomacrogol wax | 12.0 |
| Emollient-anhydrous lanolin | 5.0 |
| Emollient-mineral oil | 20.0 |
| Preservative-methylparaben | 0.15 |
| Preservative-propylparaben | 0.05 |
| Sulfactant-Duponol XL | 3.0 |
| Humectant-propylene glycol | 5.0 |
| Accelerator-thiourea | 5.0 |
| Hydroxide-strontium hydroxide | 8.21 |
| Water | 41.59 |

The other component was an aqueous solution containing 25 weight percent of guanidine carbonate.

The two components were mixed together at a weight ratio of 81:19 of relaxer cream:guanidine carbonate solution. The mixed relaxer composition was used to treat medium texture hair of Negro individuals, using the procedure of Example 1, with results generally similar to Example 1.

EXAMPLE 8

This example relates to a two-component hair relaxer formulation containing barium hydroxide. The relaxer cream component was formulated as follows:

| Ingredient | Weight Percent |
| --- | --- |
| Emulsifier-Cetomacrogol wax | 12.00 |
| Emollient-anhydrous lanolin | 5.00 |
| Emollient-mineral oil | 20.00 |
| Preservative-methylparaben | .15 |
| Preservative-propylparaben | 1.05 |
| Surfactant-Duponol XL | 5.00 |
| Hydroxide-barium hydroxide | 21.31 |
| Deionized water | 33.49 |

The other component was an aqueous solution containing 25 weight percent of guanidine carbonate.

The two components were mixed together at a weight ratio of 81:19 of relaxer cream-guanidine carbonate solution, and the mixed composition was used in laboratory tests of medium texture Negro hair swatches, following the general procedure of Example 1, with very good relaxing efficacy.

EXAMPLE 9

This example relates to a two-component hair relaxer formulation, wherein the relaxer cream had the following formulation:

| Ingredients | Weight Percent |
| --- | --- |
| Emulsifier: Brij 78 | 5.2 |
| Emulsifier: Myrj 52 | 1.3 |
| Emollient: Mineral Oil | 20.0 |
| Thickener-stearyl alcohol | 5.6 |
| Preservative-propylparaben | 0.05 |
| Preservative-methylparaben | 0.15 |
| Humectant-propylene glycol | 4.0 |
| Hydroxide-calcium hydroxide | 8.0 |
| Deionized water | 55.7 |

The other component was a 30 weight percent solution of guanidine carbonate.

The two components were mixed together in a weight ratio of 80:20 of relaxer cream-guanidine carbonate solution, and applied to the medium textured hair of Negro individuals, following the procedure of Example 1, with results similar to those obtained in Example 1.

COMPARATIVE EXAMPLE A

This example relates to the use of a formulation containing guanidine carbonate but no calcium hydroxide. Example 9 was repeated, except the calcium hydroxide was omitted from the relaxer cream, with a corresponding amount of deionized water added in lieu thereof. After the two components were mixed, the mixed composition was applied to medium texture Negro hair swatches, following the procedure of Example 1, for 20 minutes. No relaxation (or straightening) was noted.

COMPARATIVE EXAMPLE B

This comparative example relates to a formulation containing no guanidine salt, but containing calcium hydroxide. 80 parts of the relaxer cream of Comparative Example A were used, to which 6 parts of calcium hydroxide were added and thoroughly mixed. The resulting mixture was applied to medium texture Negro hair swatches, following the general procedure of Example 1, for 20 minutes, after which time no relaxation or straightening was noted.

EXAMPLE 10

A two-component aqueous hair relaxer formulation was prepared, similar to Example 2, but 5% calcium hydroxide in one component, and the other component was a 25 weight percent solution of guanidine carbonate. The components were mixed in amounts such as to produce a guanidine carbonate concentration in the resulting mixture of 3.5 percent by weight. The mixture was used to treat tresses of course Negro hair for 20 minutes treatment time, and compared with a commercial product based upon sodium hydroxide, under identical treatment conditions. The two formulations produced excellent degrees of straightening, but the formulation of the present invention was considerably less damaging to the hair. Hair treated for 20 minutes with the sodium hydroxide formulation retained about 65%–75% of its original breaking strength, wherein hair treated with the formulation of the present invention for 20 minutes retained about 90% of its original breaking strength. Thus, a wide margin exists for consumer error before damage due to overtreatment is a significant problem for the formulations of this invention.

The same two formulations were applied to the skin of rabbits, and no irritation was observed with the formulation of the present invention, after 5, 10 and 15 minutes of treatment time. In contrast, the sodium hydroxide-based commercial product resulted in minor to severe irritation at all treatment times.

EXAMPLE 11

This example relates to hair curling with a two-component formulation, wherein one component was a cream based on the following formulation:

| Ingredients | Weight Percent |
| --- | --- |
| Emulsifier-Cetomacrogol wax | 12.0 |
| Emollient-petrolatum | 7.0 |

-continued

| Ingredients | Weight Percent |
| --- | --- |
| Emollient-cocoa butter | 5.0 |
| Emollient-mineral oil | 16.0 |
| Preservative-methylparaben | .15 |
| Preservative-propylparaben | .05 |
| Surfactant-Duponol XL | 3.0 |
| Humectant-propylene glycol | 5.0 |
| Hydroxide-calcium hydroxide | 5.0 |
| Deionized water | 46.8 |

The cream formulation was prepared by heating the emollients with the propylparaben and propylene glycol to 75° C. The water and the methylparaben were heated to 75° C., and then added to the emollient mixture. The Duponol XL was added, at a temperature of approximately 60° C., and thereafter the calcium hydroxide was added to the mixture, with stirring throughout.

The other component was a 25 weight percent aqueous solution of guanidine carbonate.

The two components were mixed together, using 85 parts of the cream component and 16 parts of the guanidine carbonate solution. The formulation was used to curl medium to coarse texture brunette hair, which before the curling treatment was in a natural hair style with no permanent waving. The composition was applied to the hair to be curled and combed to distribute the formulation, with a total application time of about 2½ minutes. The hair was then rolled on curlers and an additional amount of the formulation was placed on the rolled hair. After 15 minutes total time of contact by the formulation, the hair was rinsed with water and then was shampood three times with the neutralizer shampoo of Example 1. The hair was then rerolled on curlers and dried with a blow dryer. After the treatment the hair exhibited a good tight curl.

EXAMPLE 12

Example 1 was repeated, using the two-component system of Example 11, except that the cream formulation contained 5% thiourea. The same guanidine carbonate solution was used, and the two components were mixed, using a weight ratio of 85:15 of cream component: guanidine carbonate solution. The mixed formulation was used to straighten medium texture unstraight Negro hair, for varying treatment times, following the procedure of Example 1. The treated hairs were tested for breaking strength retention, with the results set forth below:

| Treatment time, min | No. Samples | No. of Bad Breaks | Breaking Strength, g | Strength Retained, % |
| --- | --- | --- | --- | --- |
| 10 | 94 | 1 | 117 ± 6 | 99 |
| 20 | 138 | 1 | 107 ± 4 | 91 |
| 25 | 98 | — | 94 ± 4 | 80 |
| 30 | 109 | 4 | 66 ± 2 | 56 |
| Control | 57 | — | 118 ± 9 | |

For comparative purposes, a commercial product based upon sodium hydroxide was tested under identical conditions for breaking strength retention, with the results set forth below:

| Treatment time, min | No. Samples | No. of Bad Breaks | Breaking Strength, g | Strength Retained, % |
| --- | --- | --- | --- | --- |
| 10 | 93 | 2 | 114 ± 6 | 97 |

-continued

| Treatment time, min | No. Samples | No. of Bad Breaks | Breaking Strength, g | Strength Retained, % |
|---|---|---|---|---|
| 20 | 95 | — | 88 ± 5 | 75 |
| 25 | 89 | — | 75 ± 4 | 64 |
| 30 | 91 | 4 | 59 ± 2 | 50 |

EXAMPLE 14

This example relates to hair curling with a two-component formulation, with one component being in the form of a cream having the following composition:

| Ingredient | Weight Percent |
|---|---|
| Emulsifier-Cetomacrogol wax | 10 |
| Thickener-cetyl alcohol | 2.5 |
| Emollient-mineral oil | 20.0 |
| Emollient-self-emulsifiable lanolin | 3.0 |
| Preservative-propylparaben | .05 |
| Preservative-methylparaben | .15 |
| Humectant-propylene glycol | 5.0 |
| Surfactant-Duponol XL | 5.0 |
| Hydroxide-calcium hydroxide | 12.14 |
| Deionized water | 42.16 |

The other component was a 25 weight percent aqueous solution of guanidine carbonate. The two components were mixed together, in a weight ratio of 85:15 of cream component:guanidine carbonate component. The resulting formulation was applied to medium-to-fine texture brown virgin hairs. 10 hairs were wound on a 5 mm diameter glass rod and retained on the rod with tape and rubber bands. The mixed formulation was applied to the wound hairs by a spatula. The formulation was allowed to contact the hairs for 15 minutes and then the formulation was rinsed from the hairs using warm tap water for two minutes. The treated hairs were then neutralized to a pH of 6.4–6.5, again rinsed in warm tap water and blow dried for 5 minutes with a hair dryer. The hairs were removed from the glass rod by cutting in order to avoid any straightening of the curls, and allowed to remain at ambient conditions for 18 hours, after which the curls were measured for diameter and length, and the hairs were tested for breaking strength retention.

Control hairs had a breaking strength of 102±10 g, a diameter of 6.6±0.2 mm and a length of 9.8±1.1 mm. The hairs which had been treated with the two-component formulation of this example had a breaking strength of 98±9 g., corresponding to a 96% strength retention, and had a curl diameter of 5.8 mm and a length of 8.5 mm.

EXAMPLE 14

This example relates to the preparation and use of quanidine hydroxide, without using the two-component formulations of the preceding examples.

Dualite A-104, a benzyltrimethylammoniumchloride ion exhange resin manufactured by Diamond Shamrock, having a salt splitting capacity of 3.5 equivalents per kilogram, was placed in a 1 liter beaker having a magnetic stirrer. The approximately 600 g of resin were washed with 1 N NCl, filtered, rinsed several times with deionized water and then washed with a 1 N sodium hydroxide solution to convert the chloride ions on the resin to hydroxide ions. The beaker was decanted and the degree of conversion checked by adding silver nitrate to the decantate. A precipitate indicates that chloride ions are still being removed from the resins. The beaker was then decanted and the resin contained therein washed with deionized water.

The guanidine hydrochloride solution having a pH of approximately 7 was formed by dissolving 23.21 g of guanidine hydrochloride in 500 ml of deionized water. About 300 ml of the ion exchange resin prepared above, having an apparent density of 720–750 g per liter, was placed in a beaker and covered with the guanidine hydrochloride solution. After stirring for 30 minutes at room temperature, the beaker contents were decanted, with the decantage product having a pH of 12.7–12.8.

The decantate product was checked for the presence of chloride ions and no such ions were present. The solution was evaporated to dryness and analyzed, with the analysis indicating the presence of 76.19 weight percent of guanidine hydroxide.

Aqueous solutions containing varying amounts of the guanidine hydroxide were prepared by dissolving a given amount of the dry guanidine hydroxide in deionized water. The resulting solutions of guanidine hydroxide were applied to fine-to-medium texture brown virgin hair, with 10 hairs wound on a 5 mm diameter glass rod as in Example 14. The wound hairs were immersed into a guanidine hydroxide solution for 15 minutes, and then withdrawn and immediately neutralized to reduce the pH value to 6.4–6.5. The treated hairs were then blow dried, cut from the tape, and tested for curl diameter and hair length after 18 hours of exposure to ambient conditions, with the following results:

| Wt. % Guanidinium Hydroxide (corrected) | After 18 hrs | |
|---|---|---|
| | Diameter | Length |
| 7.6 | 6.6 | 7.0 |
| 15.5 | 5.0 | 6.0 |
| 38.8 | 5.0 | 6.4 |
| Control | 6.6 ± 0.2 | 9.8 ± 1.1 |

The above-noted guanidine hydroxide concentrations may not be accurate, as carbon dioxide could have been picked up from the atmosphere to form guanidine carbonate, which would in ineffective as a waving agent.

EXAMPLE 15

Example 1 was repeated, but the buffered neutralizing shampoo of that example was replaced by an acidified shampoo having the following composition:

| Ingredient | Weight Percent |
|---|---|
| Ammonium lauryl sulfate | 15 |
| Preservatives | 0.35 |
| Citric acid | to pH 5 |
| Deionized water | to 100 |

In the above formulation, the citric acid was added until the pH of the resulting shampoo had been reduced to 5.0. The results were substantially the same as reported for Example 1.

EXAMPLE 16

Guanidine hydroxide was prepared by the general procedure of Example 14, with all steps conducted under a nitrogen blanket to exclude carbon dioxide. The solution of guanidine hydroxide was freeze-dried, and then the solid guanidine hydroxide was dissolved, at a 5% by weight concentration, in water which had been boiled and then cooled under a nitrogen blanket to exclude carbon dioxide. Titration of the guanidine hydroxide solution indicated no carbonate was present.

About 25–35 medium texture kinky Negro hairs were clamped in a straightened position on a glass rod and then immersed into the room temperature solution of the guanidine hydroxide. Two tests were conducted, at 20 and 30 minutes immersion time. The quanidine hydroxide was rinsed from the hairs using warm tap water for two minutes, and then the rinsed hairs were neutralized to a pH of 6.4–6.5, rinsed again, and blown dry. Upon removal of the clamps, a noticable increase was observed in the straightening effect which was obtained in each test, compared to a control test wherein the hairs were immersed in deionized water.

What is claimed is:

1. A composition for treating hair comprising an effective amount of guanidine hydroxide as the active ingredient, the pH of said composition being at least 11.8, and said composition being applied to said hair and being removed therefrom after a predetermined amount of time.

2. A composition as claimed in claim 1 wherein the concentration of said guanidine hydroxide in said composition ranges from 2% to 20% by weight.